US009000213B2

(12) United States Patent
Bock et al.

(10) Patent No.: US 9,000,213 B2
(45) Date of Patent: Apr. 7, 2015

(54) PROCESS FOR COPRODUCING DI- AND/OR POLYISOCYANATES AND GLYCOLS

(75) Inventors: Michael Bock, Ruppertsberg (DE); Robert Baumann, Mannheim (DE); Axel Franzke, Mannheim (DE); Eckhard Stroefer, Mannheim (DE); Gerhard Theis, Maxdorf (DE)

(73) Assignee: BASF SE, Ludwigshafen (DE)

( * ) Notice: Subject to any disclaimer, the term of this patent is extended or adjusted under 35 U.S.C. 154(b) by 353 days.

(21) Appl. No.: 13/502,763

(22) PCT Filed: Oct. 27, 2010

(86) PCT No.: PCT/EP2010/066220
§ 371 (c)(1),
(2), (4) Date: Apr. 19, 2012

(87) PCT Pub. No.: WO2011/051314
PCT Pub. Date: May 5, 2011

(65) Prior Publication Data
US 2012/0209024 A1    Aug. 16, 2012

(30) Foreign Application Priority Data
Oct. 27, 2009  (EP) .................................... 09174169
Dec. 10, 2009  (EP) .................................... 09178732

(51) Int. Cl.
C07C 263/04      (2006.01)
C07C 29/12       (2006.01)
C07C 29/128      (2006.01)
C07C 68/06       (2006.01)

(52) U.S. Cl.
CPC .............. *C07C 263/04* (2013.01); *C07C 29/12* (2013.01); *C07C 29/128* (2013.01); *C07C 68/065* (2013.01); *C07C 2101/14* (2013.01)

(58) Field of Classification Search
CPC ...................................................... C07C 263/04
USPC ........................................................ 560/345
See application file for complete search history.

(56) References Cited

U.S. PATENT DOCUMENTS

| 6,080,897 | A | 6/2000 | Kawabe | |
|---|---|---|---|---|
| 6,380,419 | B2 * | 4/2002 | Kawabe | 558/277 |
| 2009/0270657 | A1 | 10/2009 | Van Der Heide et al. | |
| 2010/0130788 | A1 | 5/2010 | Coelho Tsou et al. | |
| 2010/0331564 | A1 | 12/2010 | Leitner et al. | |
| 2011/0004012 | A1 | 1/2011 | Leitner et al. | |
| 2011/0015424 | A1 | 1/2011 | Leitner et al. | |
| 2011/0178329 | A1 | 7/2011 | Bock et al. | |
| 2011/0207961 | A1 | 8/2011 | Geissler et al. | |
| 2011/0251425 | A1 | 10/2011 | Penzel et al. | |
| 2011/0263892 | A1 | 10/2011 | Breuninger et al. | |
| 2011/0313192 | A1 | 12/2011 | Rosendahl et al. | |
| 2012/0004446 | A1 | 1/2012 | Mattke et al. | |

FOREIGN PATENT DOCUMENTS

| DE | 103 49 095 | 5/2005 |
|---|---|---|
| WO | 2008 129030 | 10/2008 |
| WO | 2008 138784 | 11/2008 |
| WO | 2009 115538 | 9/2009 |

OTHER PUBLICATIONS

U.S. Appl. No. 13/479,961, filed May 24, 2012, Stroefer, et al.
U.S. Appl. No. 13/513,460, filed Jun. 1, 2012, Bock, et al.
International Search Report Issued Feb. 21, 2011 in PCT/EP10/66220 Filed Oct. 27, 2010.
U.S. Appl. No. 13/380,680, filed Dec. 23, 2011, Schelling, et al.
U.S. Appl. No. 13/394,647, filed Mar. 7, 2012, Mattke, et al.

* cited by examiner

*Primary Examiner* — Yong Chu
(74) *Attorney, Agent, or Firm* — Oblon, McClelland, Maier & Neustadt, L.L.P.

(57) ABSTRACT

A process for coproducing di- and/or polyisocyanates and glycols, comprising process stages A, B, C and E for preparing glycols and process stages A, C, D, E, F and G for preparing di- and/or polyisocyanates,
which comprises
accomplishing the material coupling via the separation of the reaction mixture obtained in process stage A into process stages B and C, by
in process stage A, reacting an aqueous alkylene oxide with carbon dioxide to give a reaction mixture comprising alkylene carbonate,
hydrolyzing a portion of the alkylene carbonate-comprising reaction mixture obtained in process stage A to glycol in process stage B,
dewatering the remaining alkylene carbonate-comprising stream of the reaction mixture from process stage A in process stage C,
in process stage D, synthesizing amine by hydrogenating an aromatic nitro compound or a nitrile,
in process stage E, transesterifying the dewatered alkylene carbonate-comprising mixture from process stage C with a monohydroxy alcohol to give the corresponding dialkyl carbonate, obtaining glycol as a coproduct,
in process stage F, reacting the dialkyl carbonate-comprising reaction mixture obtained in process stage E with the amine obtained in process stage D to a mixture comprising the corresponding mono-, di- and/or polycarbamate, which
in process stage G is cleaved to obtain the corresponding di- and/or polyisocyanate.

19 Claims, 1 Drawing Sheet

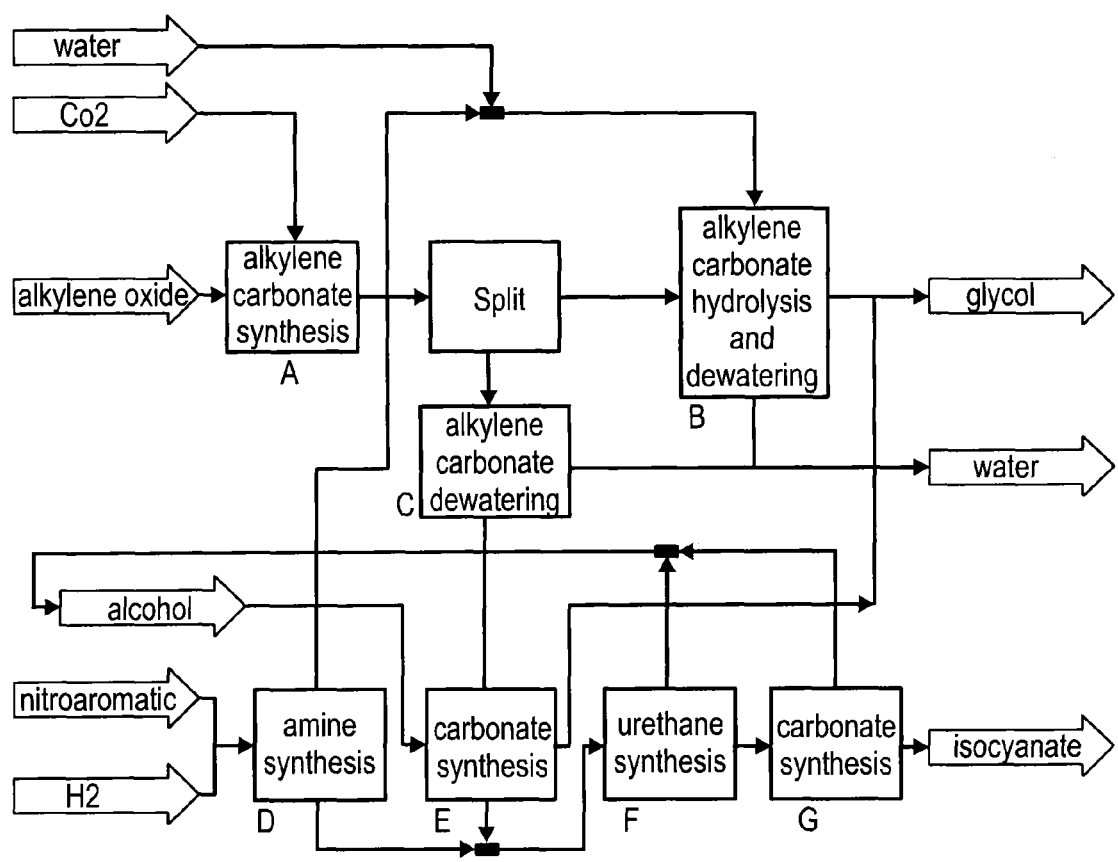

ic nitro compound or a nitrile,
PROCESS FOR COPRODUCING DI- AND/OR POLYISOCYANATES AND GLYCOLS The invention relates to a process for simultaneous production of di- and/or polyisocyanates and glycols in an integrated process.

Di- and polyisocyanates are important raw materials, in particular for the polyurethane industry. Polyisocyanates in the context of this document have a functionality of more than 2.

The conventional synthesis route for preparation of di- and/or polyisocyanates is the phosgenation of di- and/or polyamines. Especially owing to the safety problems associated with the use of phosgene, the alternative preparation route via the thermal cleavage of di- and/or polycarbamates, also known as carbamic di- or polyesters or di- or polyurethanes, is gaining increasing significance.

Di- and/or polycarbamates are prepared predominantly by reacting the corresponding dialkyl carbonates with a di- and/ or polyamine or a mixture of amines.
The di- or polyamine can be reacted with dialkyl carbonates in the presence of alkoxides as the base (see, for example, WO 2009/115538).

In this reaction, the dialkyl carbonate can be obtained by transesterifying an alkylene carbonate with a monohydroxy alcohol. In this transesterification, the corresponding alkylene glycol, referred to hereinafter as glycol for short, is obtained as a coproduct.

In addition, the alkylene carbonate can also be converted by hydrolysis to the corresponding alkylene glycol. Both products of value, alkylene glycols and di- and/or polyisocyanates, are prepared proceeding from the same reactant, the corresponding alkylene carbonate, which is in turn prepared from the corresponding alkylene oxide.

Especially at sites with world-scale alkylene oxide plants, generally with steamcrackers, it is therefore advantageous to provide integrated plants which integrate process steps for synthesis of the two coproducts above.

WO 2008/129030 describes a process for simultaneous preparation of 1,2-alkylenediols and dialkyl carbonates, wherein a 1,2-alkylene oxide is reacted with carbon dioxide in the presence of a catalyst in a loop reactor to give a gas/liquid reaction mixture, which is reacted in a second process stage with an alkanol to give a reaction mixture comprising a 1,2-alkylenediol and a dialkyl carbonate, from which the 1,2-alkylenediol and the dialkyl carbonate are removed in process stage 3. In this process, the gaseous carbon dioxide used should be utilized with maximum efficiency.

A further process for simultaneous preparation of alkylene glycol and dialkyl carbonate is known from U.S. Pat. No. 6,380,419. According to this, in a first process stage, ethylene oxide is reacted with carbon dioxide to give a mixture comprising ethylene carbonate, which in a second process stage is separated into a stream 1 comprising principally ethylene carbonate and a mixture of ethylene carbonate, ethylene glycol and water as stream 2.

Stream 1 is transesterified in a third process stage with a compound comprising a hydroxyl group to obtain the corresponding dialkyl carbonate, which is purified by distillation in a fourth process stage. The ethylene glycol obtained as a coproduct is combined with stream 2, which is hydrolyzed completely in a fifth process stage. The resulting ethylene glycol is finally purified by distillation in a sixth process stage. In this process, the mixture which comprises ethylene carbonate and is obtained by reaction of alkylene oxide with carbon dioxide is thus first purified by distillation before the transesterification to give the corresponding dialkyl carbonate.

It was accordingly an object of the invention to provide a technically simple, inexpensive process by which, proceeding from alkylene oxides, the glycol and di- and/or polyisocyanate coproducts can be obtained in a simple and inexpensive manner.

The object is achieved by a process for coproducing di- and/or polyisocyanates and glycols, comprising process stages A, B, C and E for preparing glycols and process stages A, C, D, E, F and G for preparing di- and/or polyisocyanates, which comprises
accomplishing the material coupling via the separation of the reaction mixture obtained in process stage A into process stages B and C, by
    in process stage A, reacting an aqueous alkylene oxide with carbon dioxide to give a reaction mixture comprising alkylene carbonate,
    hydrolyzing a portion of the alkylene carbonate-comprising reaction mixture obtained in process stage A to glycol in process stage B,
    dewatering the remaining alkylene carbonate-comprising stream of the reaction mixture from process stage A in process stage C,
    in process stage D, synthesizing amine by hydrogenating an aromatic nitro compound or a nitrile,
    in process stage E, transesterifying the dewatered alkylene carbonate-comprising mixture from process stage C with a monohydroxy alcohol to give the corresponding dialkyl carbonate, obtaining glycol as a coproduct,
    in process stage F, reacting the dialkyl carbonate-comprising reaction mixture obtained in process stage E with the amine obtained in process stage D to a mixture comprising the corresponding mono-, di- and/or polycarbamate, which
    in process stage G is cleaved to obtain the corresponding di- and/or polyisocyanate.

More particularly, it has been found that it is possible to feed the alkylene carbonate without complex pretreatment, by merely removing water therefrom, to the transesterification to the corresponding dialkyl carbonate. It has been found that it is sufficient merely to remove the water of reaction; depletion of the by-products which typically form in the alkylene carbonate synthesis, especially of the polyglycols which form by hydrolysis of the alkylene oxide, and removal of any homogeneous catalyst present, before the feeding into the transesterification stage is not required. The residue workup can be simplified considerably by working up the by-products and the catalyst from the alkylene carbonate synthesis together with the residue from the transesterification (of the dialkyl carbonate synthesis).

In particular, the alkylene glycol which forms in the alkylene carbonate synthesis can also be removed in the process stage of transesterification (of the dialkyl carbonate synthesis) together with the identical coproduct of the transesterification.

Thermal integration between the process stages is possible and economically viable. In the present invention, there are the following large energy sources: significant energy sources are the alkylene carbonate synthesis and the preparation of amines by hydrogenation of nitroaromatics or nitriles. Significant energy sinks are the alkali metal alkoxide synthesis, the transesterification of alkylene carbonate and the hydrolysis of alkylene carbonate to glycol when significantly more glycol than isocyanate is produced. The heats of reaction of the alkylene carbonate synthesis and amine formation by hydrogenation of nitroaromatics or nitriles can preferably be used in the urethanization for the alkali metal alkoxide synthesis and/or for the transesterification in the dialkyl carbonate synthesis. Both reactions are very energy-intensive since a shift in equilibrium by distillation in favor of the desired products takes place. It is also possible, for example, to raise 4 bar steam in these two stages from the exothermic reactions, which is then utilized in the urethanization (alkali metal alkoxide synthesis) and/or transesterification for heating of the column evaporator. It is generally possible to conduct the alkylene carbonate synthesis (WO 2008/129030) and hydrogenations to obtain the amines (e.g. WO 2008/138784 and DE 10349095) at such a temperature level that the raising of $>=4$ bar steam is possible.

Water of reaction obtained by rectification in a hydrogenation of nitroaromatics can be utilized partly for the hydrolysis of the alkylene carbonate to the glycol in the simultaneous production and/or in the protonation reaction of the metal carbamate.

Crude aqueous ethylene oxide (30-60% by weight of water) can be used for the phosgene-free preparation of di- and/or polyisocyanates via ethylene carbonate as a starting material for a dialkyl carbonate synthesis. This makes it possible to dispense with the complex, energy-intensive dewatering of the ethylene oxide, which is associated with extensive safety measures, before the reaction with carbon dioxide. The ethylene to carbonate obtained is dewatered only after the synthesis.

The carbon dioxide source for use in process stage A may especially be an offgas from an ethylene oxide synthesis, in which carbon dioxide forms through combustion of ethylene with oxygen, or else the offgas from a synthesis gas plant.

In an advantageous embodiment, process stages A, B and C can be performed at a site geographically separate from the site of process stages D to G. Such a process regime is especially attractive when the capacity of the plant for performance of process stages A, B and C is much greater compared to the capacity of the plants for the performance of the further process stages D to G.

After the dewatering, the crude mixture of the alkylene carbonate synthesis is fed directly to the carbonate synthesis. Higher-boiling by-products are not removed.

Preferably, the alkylene oxide used in process stage A is ethylene oxide and/or propylene oxide.

Preference is given to using, in process stage A, an aqueous alkylene oxide comprising 30 to 60% by weight of water.

The amine obtained in process stage D, which is reacted in process stage F with the dialkyl carbonate-comprising reaction mixture obtained in process stage E to give a mixture comprising the corresponding mono-, di- and/or polycarbamate, is preferably an individual substance or a mixture of substances or isomers thereof, selected from the following list: TDA (tolylenediamine), MDA (diaminodiphenylmethane), pMDA (polyphenylenepolymethylenepolyamine), aniline, HDA (hexamethylenediamine), IPDA (isophoronediamine), TMXDA (tetramethylenexylylenediamine), NDA (naphthylenediamine), H6TDA (hexahydrotolylenediamine), H12MDA (diaminodicyclohexylmethane) and diaminobenzene.

The monohydroxy alcohol used in process stage E is preferably an aliphatic alcohol which comprises 2 to 10 carbon atoms and optionally oxygen and/or nitrogen atoms.

Preferably, the aliphatic monohydroxy alcohol comprising 2 to 10 carbon atoms is branched, especially at the carbon atom directly adjacent to the carbon atom which bears the hydroxyl group.

In a preferred embodiment of the invention, the carbamate is removed from the reaction mixture obtained in process stage F (urethane synthesis) and condensed with formaldehyde or a formaldehyde derivative to give a mixture comprising polymers of the carbamate, from which the polycarbamates are removed and sent to process stage G (cleavage).

Advantageously, process stage F is performed in the presence of a catalyst.

Further preferably, process stage F is performed in the presence of an inert solvent.

The thermal coupling of the process stages can especially be performed by utilizing the heat of reaction from process stages A and D in one or more of process stages B, C, E and F.

Preferred variants of the energy coupling are described hereinafter.

Significant Energy Sources are 1. the alkylene carbonate synthesis (strongly exothermic) (process stage A),
2. the preparation of amines by hydrogenation of nitroaromatics (very strongly exothermic) (process stage D),
3. the waste heat of the carbamate cleavage gas G up to the dewpoint (process stage G) and
4. the heat of condensation of the alkylene carbonate dewatering (process stage C) when alkylene carbonate is partly withdrawn in gaseous form in the stripping section of the rectification for preparation of pure alkylene carbonate.

Significant Energy Sinks at Low Temperature are 1. the alkali metal alkoxide synthesis (shift in equilibrium, very high steam requirement) (process stage F, part of the urethanization),
2. the transesterification of alkylene carbonate to dialkyl carbonate (shift in equilibrium, very high steam requirement) (process stage E),
3. the hydrolysis of alkylene carbonate to glycol (endothermic) (process stage B),
4. the separation of water and glycol after the hydrolysis when significantly more glycol than isocyanate is produced (process stage B), and
5. the heating of the bottoms in the dewatering of the alkylene carbonate (process stage C).

The abovementioned energy sinks typically work at least 10° C. below the energy sources mentioned. The energy can thus be transferred. As well as the material coupling, there is thus also an advantageous energy coupling between the process stages.

Advantageously, at least a portion of the heat of reaction of the alkylene carbonate synthesis (process stage A) can be utilized for alkali metal alkoxide synthesis in the urethanization (process stage F).

Advantageously, at least a portion of the heat of reaction of the alkylene carbonate synthesis (process stage A) can be utilized for transesterification of the alkylene carbonate (process stage E).

Advantageously, at least a portion of the heat of reaction of the amine formation by hydrogenation (process stage D) can be utilized for alkali metal alkoxide synthesis in the urethanization (process stage F).

Advantageously, at least a portion of the heat of reaction of the amine formation by hydrogenation (process stage D) can be utilized for transesterification of the alkylene carbonate (process stage E).

Advantageously, at least a portion of the heats of condensation of an alkylene carbonate dewatering (process stage C) can be utilized in the alkali metal alkoxide synthesis in the urethanization (process stage F).

More particularly, at least a portion of the heat of reaction of the alkylene carbonate synthesis (process stage A) can be used in the carbamate cleavage (process stage G).

Advantageously, at least a portion of the heat of reaction of the amine formation by hydrogenation (process stage D) can be used for heating of the alkylene carbonate hydrolysis (process stage B) and/or the dewatering of the alkylene carbonate (process stage C).

The invention is illustrated in detail hereinafter by FIG. 1 and a working example for the illustrative case of the coproduction of ethanediol (($CH_2OH)_2$) and tolylene diisocyanate (TDI) from ethylene oxide (EO) and dinitrotoluene (DNT).

WORKING EXAMPLE

Stages A to C, E 53200 kg/h of aqueous ethylene oxide (44.8% by weight of water) are reacted at 110° C. with 34186 kg/h of carbon dioxide in the presence of a strongly basic anion exchanger to give ethylene carbonate and ethanediol (process stage A). 50% of the crude product are transferred into process stage C and 50% of the crude product into process stage B. As a side reaction in process stage A, there is formation of ethanediol and higher glycols.

In process stage B, after hydrolysis and dewatering, 20298 kg/h of ethanediol are formed.

The unhydrolyzed reaction output removed from process stage A (42099 kg/h, 66.7% by weight of ethylene carbonate) is dewatered without removing the polymeric by-products of the synthesis. The dewatered ethylene carbonate is then reacted at 160° C. in the presence of 1 mol % of sodium isobutoxide in a tubular reactor with 25942 kg/h of isobutanol to give 54014 kg/h of diisobutyl carbonate and 19250 kg/h of ethanediol (process stage E). Unconverted components (such as ethylene carbonate and isobutanol) are recycled into the equilibrium reactor via a vacuum distillation. The products (diisobutyl carbonate and ethanediol) are likewise separated from one another by distillation under reduced pressure.

The combined residues of process stage A and process stage E are discharged together into process stage E.

The ethanediol formed in small amounts by the partial hydrolysis of ethylene oxide in process stage A is likewise discharged here (process stage E) with the ethanediol formed additionally as a coproduct in the transesterification of ethylene carbonate to diisobutyl carbonate and combined with the ethanediol from process stage B.

Stage D 29870 kg/h of technical grade dinitrotoluene (DNT) are converted at 180° C. using 2180 kg/h of hydrogen to 18936 kg/h of technical grade tolylenediamine (TDA). 385 kg/h of high-boiling by-products are removed from the TDA after prior dewatering in a dividing wall column.

Stage F

Process stage F consists of the urethanization and alkali metal alkoxide preparation. For this purpose, 24878 kg/h of 50 w % sodium hydroxide solution are reacted with 120639 kg/h of isobutanol at 90° C. in a reaction column with discharge of water to give a total of 29860 kg/h of sodium isobutoxide dissolved in isobutanol (20 w % solution). The diisobutyl carbonate obtained in stage E (54014 kg/h) is reacted with these 29860 kg/h (calc. 100%) of sodium isobutoxide in isobutanol (20% by weight) and 18936 kg/h of TDA melt from stage D at 120° C. (process stage F, step 1) and reacted in a subsequent hydrolysis with water at 50° C. to give 49975 kg/h of tolylene bis(O-isobutylcarbamate) (process stage F, step 2). The reaction mixture from step 2 of stage F is, after an extractive removal of the sodium hydroxide solution, subsequently separated by distillation of the organic phase into dicarbamate, diisobutyl carbonate and isobutanol. Sodium hydroxide solution and isobutanol are correspondingly recycled into the isobutoxide synthesis and the transesterification.

Stage G

The carbamate is metered into a fluidized bed as a melt at 130° C. and cleaved at 400° C. to tolylene diisocyanate (TDI) and alcohol, using nitrogen as the fluidizing gas (process stage G). The gaseous product mixture is cooled in a liquid quench below the dewpoint of TDI and then separated by distillation under reduced pressure into TDI, isobutanol and quench medium. Isobutanol is recycled.

Thus, a total of 25143 kg/h of TDI and 39548 kg/h of ethanediol are formed as products of value.

There follows a description of the energy coupling of the process. Significant energy sources at relatively high temperature are
1. the ethylene carbonate synthesis (strongly exothermic, 110° C.) (stage A)
2. the preparation of TDA by hydrogenation of DNT (very strongly exothermic, 180° C.) (stage D)
3. the waste heat of the carbamate cleavage gas in the quench up to the dewpoint (stage G) and
4. the heat of condensation of the ethylene carbonate dewatering (stage C) with removal of gaseous ethylene carbonate as a by-product at an operating pressure of 100 mbar abs or less (to 30 mbar)

Significant Energy Sinks at Relatively Low Temperature are
a. the sodium isobutoxide synthesis (very high steam requirement, 90° C.) (stage F),
b. the transesterification of ethylene carbonate to diisobutyl carbonate (very high steam requirement) (stage E). Ethylene carbonate is preheated to reaction temperature 160° C. (possible: 100 to 160° C.). Operation of two rectification columns for purifying distillation of diisobutyl carbonate and ethanediol each at less than 300 mbar abs.
c. the hydrolysis of ethylene carbonate to ethanediol (endothermic, below 160° C., see U.S. Pat. No. 6,080,897, example 3, column 10) (stage B),
d. the separation of water and ethanediol after the hydrolysis, see U.S. Pat. No. 6,080,897, example 3, column 10 (stage B) and
e. the heating of the column bottom in the dewatering of the ethylene carbonate, since it is conducted at a pressure of 100 mbar abs or less (to 30 mbar) (stage C).

The abovementioned energy sinks work at least 10° C. below the energy sources mentioned. The energy can thus be transferred. As well as the material coupling, there is thus also an advantageous energy coupling between the individual process stages.

Advantageously, the following integrated heat system can thus be implemented:

Source 2 (steam from the DNT hydrogenation) is used fully or partly for heating of sinks a, b, c, d and/or e.
Source 1 (waste heat from the ethylene carbonate synthesis) is used fully or partly for heating of sink a.
Source 3 (waste heat from quench/cooling of the carbamate cleavage gas) is used fully or partly for heating of sink b.
Source 4 (waste heat from dewatering in the case of gaseous side draw removal) is used fully or partly for heating of sink a.

FIG. 1 shows the schematic illustration of a preferred plant for performance of the process according to the invention.

In process stage A, an aqueous alkylene oxide, for example aqueous ethylene oxide (EO), is reacted with carbon dioxide to give a reaction mixture comprising alkylene carbonate.

The reaction mixture which comprises the alkylene carbonate and is obtained in process stage A is split into a stream which is hydrolyzed in process stage B to glycol, for example ethanediol (($CH_2OH$)$_2$), and into another stream which is dewatered in process stage C.

In process stage D, by hydrogenation of an aromatic nitro compound, for example dinitrotoluene (DNT), an amine is synthesized, for example tolylenediamine (TDA).

In process stage E, the dewatered mixture comprising the alkylene carbonate from process stage C is transesterified with a monohydroxy alcohol, for example isobutanol, to the corresponding dialkyl carbonate, with coproduction of glycol, for example ethanediol (($CH_2OH$)$_2$).

In process stage F, the reaction mixture which comprises the dialkyl carbonate and is obtained in process stage E is reacted with the amine obtained in process stage D to give a mixture comprising the corresponding carbamate, which is cleaved in process stage G to obtain the corresponding isocyanate, for example tolylene diisocyanate (TDI).

The invention claimed is:

1. A process for coproducing (i) at least one isocyanate selected from the group consisting of a diisocyanate and a polyisocyantate and (ii) a glycol, the process comprising:
   (A1) reacting an aqueous alkylene oxide comprising 30 to 60% by weight of water, based on a total weight of the aqueous alkylene oxide, with carbon dioxide, to obtain first reaction mixture comprising alkylene carbonate; then
   (A2) separating the first reaction mixture into a first and second stream comprising the alkylene carbonate; then
   (B) hydrolyzing the first stream, to obtain a glycol;
   (C) dewatering the second stream, to obtain a dewatered stream;
   (D) hydrogenating an aromatic nitro compound or a nitrile, to obtain (d) an amine;
   (E) transesterifying the dewatered stream with a monohydroxy alcohol, to obtain a second reaction mixture comprising a dialkyl carbonate and the glycol; and then
   (F) reacting the second reaction mixture with the amine (d), to produce a third reaction mixture comprising at least one carbamate selected from the group consisting of a monocarbamate, a dicarbamate, and a polycarbamate;
   (G) cleaving the carbamate in the third reaction mixture, to obtain the diisocyanate, polyisocyanate, or both.

2. The process of claim 1, wherein the alkylene oxide in (A) is at least one selected from the group consisting of ethylene oxide and propylene oxide.

3. The process of claim 1, wherein the amine (d) is at least one substance or an isomer thereof selected from the group consisting of: TDA (tolylenediamine), MDA (diaminodiphenylmethane), pMDA (polyphenylenepolymethylenepolyamine), HDA (hexamethylenediamine), IPDA (isophoronediamine), TMXDA (tetramethylenexylylenediamine), NDA (naphthylenediamine), H6TDA (hexahydrotolylenediamine), H12MDA (diaminodicyclohexylmethane), and diaminobenzene.

4. The process of claim 1, wherein the monohydroxy alcohol in (E) is an aliphatic alcohol comprising 2 to 10 carbon atoms and optionally comprising at least one selected from the group consisting of an oxygen atom and a nitrogen atom.

5. The process of claim 4, wherein the aliphatic monohydroxy alcohol is branched.

6. The process of claim 1, further comprising, after (F):
   removing the carbamate from the third reaction mixture and condensing the carbamate with formaldehyde or a formaldehyde derivative, to obtain a fourth reaction mixture comprising polycarbamates; and then
   removing the polycarbamates from the fourth reaction mixture and cleaving the polycarbamates in (G).

7. The process of claim 6, wherein the amine (d) is aniline.

8. The process of claim 1, wherein the reacting (F) is performed in the presence of a catalyst.

9. The process of claim 1, wherein the reacting (F) is performed in the presence of an inert solvent.

10. The process of claim 1, wherein the heat of reaction from the reacting (A) and the hydrogenating (D) is utilized in at least one selected from the group consisting of the hydrolyzing (B), the dewatering (C), the transesterifying (E), and the reacting (F).

11. The process of claim 5, wherein the aliphatic monohydroxy alcohol is branched at the carbon atom directly adjacent to the carbon atom bearing the hydroxyl group.

12. The process of claim 2, wherein the alkylene oxide in (A) is ethylene oxide.

13. The process of claim 2, wherein the alkylene oxide in (A) is propylene oxide.

14. The process of claim 2, wherein the alkylene oxide in (A) is ethylene oxide and propylene oxide.

15. The process of claim 10, wherein a portion of the heat of reaction from the reacting (A) is utilized in the reacting (F).

16. The process of claim 10, wherein a portion of the heat of reaction from the reacting (A) is utilized the transesterifying (E).

17. The process of claim 10, wherein a portion of the heat of reaction from the hydrogenating (D) is utilized in the reacting (F).

18. The process of claim 10, wherein a portion of the heat of reaction from the hydrogenating (D) is utilized in the transesterifying (E).

19. The process of claim 10, wherein a portion of the heat of reaction from the hydrogenating (D) is utilized in at least one selected from the group consisting of the hydrolyzing (B) and the dewatering (C).

* * * * *